United States Patent [19]

Kawakami et al.

[11] Patent Number: 4,668,771
[45] Date of Patent: May 26, 1987

[54] METHOD FOR SEPARATING BOVINE LACTOFERRIN FROM COW'S MILK AND PURIFYING SAME

[75] Inventors: Hiroshi Kawakami; Hiroshi Shinmoto, both of Kawagoe; Shunichi Dosako, Urawa; Kenkichi Ahiko, Tokyo, all of Japan

[73] Assignee: Snow Brand Milk Products Co., Ltd., Japan

[21] Appl. No.: 808,899

[22] Filed: Dec. 13, 1985

[30] Foreign Application Priority Data

Dec. 19, 1984 [JP] Japan .................................. 59-266401

[51] Int. Cl.⁴ .......................... A23J 1/20; C07K 15/06
[52] U.S. Cl. ......................................... 530/366; 424/85; 514/21; 530/395; 530/399; 530/413; 530/832; 530/809; 435/68; 435/172.3; 435/240; 435/241

[58] Field of Search ............... 530/366, 399, 413, 809, 530/832; 424/85; 514/21; 435/172.3, 240, 241, 68

[56] References Cited

U.S. PATENT DOCUMENTS 4,229,342 10/1980 Mirabel .......................... 530/366 X
4,436,658 3/1984 Peyrouset et al. .............. 530/366 X

*Primary Examiner*—Howard E. Schain
*Attorney, Agent, or Firm*—McGlew and Tuttle

[57] ABSTRACT

This invention discloses a method for separating a highly pure form of bovine lactoferrin from cow's milk and purifying same which comprises preparing an affinity-chromatographic column by fixing a monoclonal antibody against bovine lactoferrin to an insoluble carrier; passing milk or a solution of bovine lactoferrin derived from cow'milk through the affinity-chromatographic column; and then eluting the bovine lactoferrin adsorbed to the affinity-chromatographic column.

5 Claims, No Drawings

METHOD FOR SEPARATING BOVINE LACTOFERRIN FROM COW'S MILK AND PURIFYING SAME

BACKGROUND OF THE INVENTION

1. Field of the Invention:

This invention relates to a separation and purification method for obtaining bovine lactoferrin from cow's milk in a highly pure state and in high yield.

Lactoferrin is an iron-binding protein found in externally secreted fluids such as milk. It is not only highly beneficial in the feeding of infants from a nutritional point of view, but also has the physiological effect of exerting a bacteriostatic action on pathogenic bacteria occurring in the intestines and exhibiting a high degree of iron requirement because of its characteristic iron-binding ability. In other word, lactoferrin may be said to be an important milkprotein which not only serves as a nutrient but also has a pharmacological significance as an antiinfective agent, similar to immunoglobulins and lysozyme present in milk.

2. Description of the Prior Art:

Conventionally, in view of the above characteristic properties of lactoferrin, a number of methods for separating lactoferrin from milk and purifying it have been proposed. However, since lactoferrin is a protein having a highly reactive molecular structure and is also apt to interact with other milkproteins, it has been difficult to isolate a highly pure form of lactoferrin easily and effectively according to the conventional methods.

For example, one conventional method for separating and purifying lactoferrin comprises providing skim milk from which fat has been separated, removing casein therefrom by isoelectric precipitation at pH 4.6, salting out the resulting whey fraction with ammonium sulfate, dialyzing the resulting fraction against deionized water, and then passing the retentate several times through an ion exchange resin (Gordon, Ziegler, Bash et al.: Biochim. Biophys. Acta, 60, 410–411, 1962; Merton L. Glove et al.: Biochim. Biophys. Acta, 100, 154–162, 1965; Johansson, B. G. et al.: Acta Chem. Scand., 23, 683, 1969). In addition, modifications of the above method include a method in which silica particles are used in place of the ion exchange resin (Japanese patent Laid-Open No. 28233/'83) and a method in which, after the retentate is passed through an ion exchange resin, the resulting product is further subject to copper affinity chromatography (Norihiro Kawakata, Yoshio Yoshino et al., Abstracts of Lectures at the 1983 Annual Meeting of the Japan Biochemical Society, p. 1053). However, these methods are all lacking in practical utility because they require complicated operations and an unduly long treating time Moreover, since lactoferrin has the property of interacting with other proteins present in milk, the above methods using an ion exchange resin cannot avoid contamination of the product with immunoglobulins and other proteins present in milk. Accordingly, it is difficult in practice to obtain a highly pure form of lactoferrin. In addition, these methods are also disadvantageous in that the repeated treatment by salting-out and ion exchange not only causes a marked reduction in the recovery of lactoferrin but also makes it practically impossible to recover and reuse milkproteins other than lactoferrin and other milk components present in the residues obtained during the course of the separation and purification of lactoferrin.

SUMMARY OF THE INVENTION

In consideration of the above problems encountered in the prior art methods for isolating a highly pure form of lactoferrin from cow's milk, the present inventors have conducted research with a view to establishing a separation and purification method which can be advantageously used for the isolation of bovine lactoferrin from cow's milk in a highly pure state and in high yield. As a result, the present inventors found that bovine lactoferrin can specifically combine with and become adsorbed to an affinity-chromatographic column having fixed thereto a monoclonal antibody against bovine lactoferrin, and succeeded in obtaining a highly pure form of bovine lactoferrin in high yield by separating bovine lactoferrin from cow's milk and purifying it with the aid of such an affinity-chromatographic column.

Accordingly, it is the primary object of the present invention to provide a separation and purification method for obtaining a highly pure form of bovine lactoferrin from cow's milk in high yield.

Other objects of the present invention will be apparent from the following description.

These and other objects of the present invention are accomplished by a method for separating a highly pure form of bovine lactoferrin from cow's milk and purifying same which comprises preparing an affinity-chromatographic column by fixing a monoclonal antibody against bovine lactoferrin to an insoluble carrier; passing cow's milk or a solution of bovine lactoferrin derived from cow's milk through the affinity-chromatographic column; and then eluting the bovine lactoferrin adsorbed to the affinity-chromatographic column.

DETAILED DESCRIPTION OF THE INVENTION

The method of the present invention is characterized in that an affinity-chromatographic column comprising an insoluble carrier having fixed thereto a monoclonal antibody against bovine lactoferrin is used to separate bovine lactoferrin from cow's milk and purify same.

Thus, the method of the present invention is a method for separating and purifying lactoferrin by the utilization of biological affinity (i.e., highly specific interaction between biological components), and is essentially different from conventional separation methods utilizing physical or chemical affinity.

A monoclonal antibody against bovine lactoferrin for use in the present invention can be obtained as follows: A hybridoma capable of producing a monoclonal antibody against bovine lactoferrin is formed by fusing spleen lymphocytes (hereinafter referred to as spleen cells) from a bovine lactoferrin-immunized mouse with mouse myeloma cells (hereinafter referred to as myeloma cells). Then, according to any well-known technique, the hybridoma is injected into the abdominal cavity of mice and their ascitic fluid is recovered. Alternatively, the hybridoma is cultured in a suitable medium and its supernatant is recovered. The recovered ascitic fluid or supernatant is then purified by precipitation with ammonium sulfate and treatment with an anion exchange resin to obtain the desired antibody.

First, a concrete example of the method for preparing a monoclonal antibody against bovine lactoferrin will be explained below.

As stated above, a monoclonal antibody against bovine lactoferrin can be produced by culturing a hybridoma which is obtained by fusing spleen cells from a bovine lactoferrin-immunized mouse with myeloma cells. Such a hybridoma can be formed, for example, according to the following procedure. (The aforesaid method for forming such a hybridoma is disclosed and claimed in an application for an independent patent by the same inventors.)

Formation of a Hybridoma Capable of Producing a Monoclonal Antibody Against Bovine Lactoferrin Bovine lactoferrin is isolated from the whey fraction of milk according to a well-known procedure (for example, Johansson, B. G. et al.: Acta Chem. Scand., 23, 683, 1969) and then a solution thereof is prepared (usually by using a phosphate buffer saline solution (PBS), pH 7.2, containing 0.15 M sodium chloride). This solution is mixed with an equal amount of Freund's complete adjuvant to form an emulsion. By injecting this emulsion into its abdominal cavity, a mouse (usually aged 6 to 8 weeks) is immunized three times at intervals of 2 weeks. The bovine lactoferrin used for this purpose may contain small amounts of impurities. However, in order to obtain the desired hybridoma, it is naturally preferable to use a highly pure form of bovine lactoferrin.

No particular limitation is placed on the type of mouse used in the present invention. However, it is usually desirable to use a BALB/C strain mouse.

From the mouse immunized in the above-described manner, the spleen is preferably excised 6 or 7 days after the final immunization with bovine lactoferrin. This is because the rate of formation of desired hybridomas is enhanced by using spleen cells collected from the spleen so excised.

No particular limitation is placed on the type of myeloma cells to be fused with the spleen cells obtained in the above manner. However, where it is desired to fuse them with spleen cells obtained from a BALB/c strain mouse, it is preferable to use SP2/O-Ag14 cells which do not secrete the K chain of IgG. The fusion may be carried out according to any well-known procedure. However, where SP2/O-Ag14 cells are used as the myeloma cells, it is essential that the fusion time including the addition of a fusion promoter (fusion inducer), mixing and dilution should be in the range of 5 to 15 minutes, and preferably 9 to 11 minutes. In this connection, if the fusion time is in the range of 9 to 11 minutes, the rate of colony formation will approach almost 100%. Where spleen cells from a BALB/c strain mouse immunized with bovine lactoferrin are fused with SP2/O -Ag14 cells, the rate of colony formation (the rate of fusion) can be greatly enhanced by using gas-chromatographic grade polyethylene glycol (M.W. 4000; Merck & Co., Inc.) as a fusion promoter at a concentration of 50%.

After completion of the fusion, the fused cells may be treated in the conventional manner. Specifically, the fused cells are dispersed in an HT medium (Dulbecco-modified MEM medium containing hypoxanthine, thymidine and 10% fetal calf serum), sprayed over a 96-hole microtiter plate and cultured at a temperature of 37° C. under an atmosphere of 5% carbon dioxide. From the following day, selection of hybridomas is carried out in an HAT medium (Dulbecco-modified MEM medium containing hypoxanthine, aminopterine, thymidine and 10% fetal calf serum).

As soon as the colonies have grown to a sufficient size, the hybridomas are screened according to the solid phase method. Then, the hybridomas exhibiting a positive reaction are cloned according to the limiting dilution method.

In one embodiment, the solid phase method is carried out by causing a soluble antigen to be adsorbed to a 96-hole soft microwell, treating the wells with bovine serum albumin (BSA) to block the portions to which the antigen is not adsorbed, and placing the supernatants of the aforesaid culture media in the wells to effect reaction with the antigen. Upon completion of the reaction, the wells are washed thoroughly and antibodies against biotinylated mouse antibodies are added thereto as secondary antibodies. Thereafter, the wells are treated with avidin and fluorescein-labeled biotin to detect the desired antibody by the production of fluorescence.

In another embodiment, the limiting dilution method is carried out as follows: A dispersion of $10^8$ mouse thymus cells and 50 hybridoma cells in 10 ml of an HT medium is sprayed over a 96-hole microtiter plate so that one hybridoma cell or less is present in each well and, hence, single colonies of the hybridoma will be formed. The mouse thymus cells are added as feeder cells because hybridoma cells cannot grow at low cell densities.

The above cloning procedure is repeated three or more times to obtain a monocloned hybridoma.

Preparation of a Monoclonal Antibody Against Bovine Lactoferrin

The hybridoma formed in the above manner is injected into the abdominal cavity of mice and their ascitic fluid is recovered. Alternatively, the hybridoma is cultured in a suitable medium and its supernatant is recovered. The recovered ascitic fluid or supernatant is then purified by precipitation with ammonium sulfate and ion exchange chromatography to obtain a monoclonal antibody against bovine lactoferrin.

In one embodiment, the monoclonal antibody against bovine lactoferrin can be prepared as follows: cells of the aforesaid hybridoma are dispersed in a PBS and injected into the abdominal cavity of BALB/c strain mice to which pristan (2,6,10,14-tetramethylpentadecane) has previously been administered. After 7 to 10 days, their ascitic fluid is collected, cleared by centrifugation, diluted with PBS so as to give a protein concentration of the order of 10 to 12 mg/ml, and then salted out with 45% saturation ammonium sulfate. A solution of the resulting precipitate fraction is dialyzed and then purified by ion exchange chromatography.

Then, the monoclonal antibody against bovine lactoferrin thus obtained may be used in the separation and purification of bovine lactoferrin. This can be accomplished by preparing an affinity-chromatographic column of the antibody according to the procedure described below and passing a solution of crude bovine lactoferrin obtained from cow's milk through the affinity-chromatographic column.

Preparation of an Affinity-Chromatographic Column

The monoclonal antibody against bovine lactoferrin prepared in the above manner is mixed with an equal amount of an insoluble carrier such as a carrier for use in affinity chromatography (for example, affigel-10; Bio-Rad Co.) and this mixture is stirred at low temperature to bind and fix the antibody to the carrier. After washing, those functional groups on the carrier to which the aforesaid antibody is not attached are inactivated and the carrier is then washed. The resulting affinity gel is packed into a column of suitable size to form an affinity-chromatographic column.

In this connection, a carrier (such as an affinity gel) having fixed thereto a monoclonal antibody against bovine lactoferrin can be preserved at a temperature of 4° C. for about 3 months or more, provided that it is kept dispered in a PBS, containing 0.02% sodium azide.

Separation and Purification of Bovine Lactoferrin

In order to separate bovine lactoferrin from cow's milk and purify it by using an affinity-chromatographic column prepared by fixing a monoclonal antibody against bovine lactoferrin to an insoluble carrier in the above manner, an appropriate amount of a bovine lactoferrin-containing sample (such as cow's milk) is passed through the affinity-chromatographic column at a temperature of 50° C. or below, preferably at room temperature. After the fraction not adsorbed to the column is allowed to flow out, the column is washed with a PBS containing 0.5 M sodium chloride and then with a 0.15 M sodium chloride solution. Thereafter, the bovine lactoferrin adsorbed to the column is eluted by passing therethrough an acetate solution having a pH of 4.7 or less, preferably a pH of 4.3 to 2.7, and containing 0.15 M sodium chloride. The pH of the resulting bovine lactoferrin fraction is immediately returned to neutrality by the addition of alkali.

The raw milk used for the separation of bovine lactoferrin can be any of various types of cow's milk including colostrum, transitive milk, normal milk, and late milk. However, colostrum and late milk are preferred from the viewpoint of recovery rate. Moreover, bovine lactoferrin may also be recovered from pasteurized milk, whey, pasteurized whey, and from milk powders such as whey protein concentrate (WPC).

When bovine lactoferrin is separated from cow's milk and purified according to the method of the present invention using an affinity-chromatographic column having fixed thereto a monoclonal antibody against bovine lactoferrin, it is possible to eliminate all the pretreatments required in the conventional methods, including the separation of casein with an acid, salting-out with ammonium sulfate, dialysis and freeze-drying. Moreover, in the conventional methods, the raw milk subjected to the aforesaid pretreatments must be passed several times through an ion exchange resin. In the method of the present invention, however, bovine lactoferrin can readily be separated from other milk components by passing cow's milk through an affinity-chromatographic column only once.

Furthermore, an affinity-chromatographic column having fixed thereto a monoclonal antibody against bovine lactoferrin is useful in the separation of bovine lactoferrin alone, and has no affinity for lactoferrins derived from milk of mammals of different species, for example, human lactoferrin. In other words, the specificity of such affinity-chromatographic columns is so high that an affinity-chromatographic column having fixed thereto a monoclonal antibody against human lactoferrin is effective in the separation of human lactoferrin alone and an affinity-chromatographic column having fixed thereto a monoclonal antibody against bovine lactoferrin is effective in the separation of bovine lactoferrin alone.

In addition, the conventional methods produce lactoferrin having a purity of at most 66% or so, and its recovery is of the order of 60%. According to the method of the present invention, however, a highly pure form of bovine lactoferrin having a purity of 98% or greater can be obtained by a single passage through a column, and with a high recovery of not less than 80%, even 90%.

The purity and recovery of bovine lactoferrin given herein have been estimated according to the following procedures.

SDS electrophoresis of the recovered bovine lactoferrin fraction gave a single perfect band. However, it cannot be concluded from this electrophoretic analysis that the purity of lactoferrin is 100%, because lactoperoxidase having substantially the same molecular weight (about 80,000) as lactoferrin is present in cow's milk. Separately, an immunological double diffusion test between anti-lactoperoxidase serum and the bovine lactoferrin fraction revealed that no precipitin line was formed. Thus, the content of lactoperoxidase which may be present in the bovine lactoferrin fraction can be estimated to be no more than 0.01%. This is because the bovine lactoferrin fraction must contain 0.01% or more of lactoperoxidase in order to form such a precipitin line.

Accordingly, on the basis of the results obtained by the above SDS electrophoresis, immunological double diffusion test, and measurement of the protein concentration of the bovine lactoferrin fraction, the purity of the bovine lactoferrin obtained by method of the present invention has been judged to be 98% or higher.

As for the recovery, an immunological double diffusion test between anti-bovine lactoferrin serum and the non-adsorbed fraction revealed that no precipitin line was formed. Thus, the content of residual bovine lactoferrin in the non-adsorbed fraction can be judged to be no more than 0.01%. This is because the non-adsorbed fraction must contain 0.01% or more of bovine lactoferrin in order to form such a precipitin line.

Accordingly, on the basis of the results obtained by the above immunological double diffusion test and protein concentration measurement, the recovery of bovine lactoferrin in the method of the present invention can be judged to be at least 80% or greater, even 90% or greater.

The lactoferrin separated and purified by the method of the present invention has the following advantages.

As stated above, lactoferrin has the physiological effect of exerting a strong growth-inhibiting action on iron-requiring pathogenic bacteria because of its iron-binding ability. Accordingly, in order to utilize its physiological effect, the recovered lactoferrin must not be saturated with iron, but must retain its iron-binding ability. However, the lactoferrin recovered by conventional methods can sometimes be an iron-bound lactoferrin assuming a pink color (see Japanese Patent Laid-Open No. 28233/'83). In such a case, the aforesaid physiological effect cannot be anticipated unless the lactoferrin is treated with an iron-chelating agent (such as EDTA) to get rid of the iron.

By contrast, the lactoferrin separated and purified by the method of the present invention retains its inherent iron-binding ability perfectly. Parenthetically, the iron-binding abilities of bovine lactoferrin samples obtained by the method of the present invention were determined according to the procedure of Suzuki, Nonaka et al. ("Eiyo-to-Shokuryo", Vol. 31, No. 4, 395–403, 1978). As a result, their iron-binding abilities of the samples were found to range from 2.4 to 3.7 mg per gram of lactoferrin, attesting that the bovine lactoferrin obtained by the method of the present invention retains its inherent iron-binding ability perfectly.

Accordingly, the bovine lactoferrin obtained by the method of the present invention can be used as a preventive for protecting infants against infection caused by iron-requiring pathogenic bacteria and as a remedy for various symptoms arising from such pathogenic bacteria and, moreover, can also be added to milk powder for infant feeding to approximate its protein composition to that of breast milk and to enhance the aforesaid anti-infective ability of the milk powder.

Furthermore, it is known that human and bovine lactoferrins can act as growth factors for specific types of cells (Biochim. Biophys. Acta, 763, 377, 1983). While the growth-promoting effect of human lactoferrin is noted only on human B and T lymphocytes, bovine lactoferrin has a growth-promoting effect not only on those cells but also on mouse lymphocytes. For this reason, bovine lactoferrin makes it possible to make an effective cell culture for such cells by adding it to the culture medium.

The present invention is further illustrated by the following examples. However, these examples are not to be construed to limit the scope of the invention.

EXAMPLE 1

Formation of a Hybridoma Capable of Producing a Monoclonal Antibody Against Bovine Lactoferrin Bovine lactoferrin (60% pure) which had been obtained according to the conventional ion exchange method was dissolved in a phosphate buffer saline solution (PBS), pH 7.2, containing 0.15 M sodium chloride so as to give a concentration of 0.3%. This solution was rixed with an equal amount of Freund's complete adjuvant (Difco) to form an emulsion. A BALB/c strain mouse, aged 6 to 8 weeks, was immunized by injecting the emulsion into its abdominal cavity. This immunization was repeated three times at intervals of 2 weeks. Six days after the final immunization, the spleen was excised from the mouse and spleen cells were collected therefrom. These speen cells were dispersed in a DMEM (Dulbecco-modified minimum essential medium) and mixed with SP2/O-Ag14 mouse myeloma cells in a ratio of 2:1. To this mixture was added a 50% solution of polyethylene glycol (gas-chromatographic grade M.W. 4000; Merck & Co., Inc.) as a fusion promoter. Thus, fusion of the cells was completed in 10 minutes. The resulting fused cells were separated from the polyethylene glycol by centrifugation, dispersed in an HT medium so as to give a cell density of $1 \times 10^7$ cells/ml or less, sprayed over 96-hole microtiter plates, and cultured at 37° C. under an atmosphere of 5% carbon dioxide. From the day after the commencement of the culture(designated as the first day), half the medium was continually exchanged with an HAT medium. On the 17th day, hybridomas were screened according to the solid phase method. As a result, 99% of the hybridomas formed a colony, while 8.3% of the hybridomas exhibited a positive reaction for bovine lactoferrin.

Then, the hybridomas exhibiting a positive reaction were transferred to 24-hole microtiter plates, kept in culture in an HT medium and cloned as soon as they grew to a cell density of $1 \times 10^5$ cells/ml. Thereafter, they were cultured in an HT medium for 2 weeks and the hybridomas forming a single colony in the well were subjected to secondary cloning.

This cloning and screening procedure was repeated three times. Thus, there were obtained monoclones of a hybridoma capable of producing an antibody against bovine lactoferrin.

A stock of the resulting hybridoma capable of producing a monoclonal antibody against bovine lactoferrin is maintained in Axerican Type Culture Collection, 12301 Parklawn Drive, Rockville, Md. 20852-1776 under Deposition No. ATCC HB 8852.

Preparation of a Monoclonal Antibody Against Bovine Lactoferrin

Cells of the aforesaid hybridoma capable of producing a monoclonal antibody against bovine lactoferrin were dispersed in PBS so as to provide a dose of $10^7$ cell/0.5 ml for each mouse, and injected into the abdominal cavity of 18 BALB/c strain mice to which pristan (2,6,10,14-tetramethylpentadecane) had previously been administered.

Seven to ten days after the aforesaid injection, 86 ml of ascitic fluid was collected, cleared by centrifugation, diluted with PBS so as to give a protein concentration of 10 to 12 mg/ml, and then salted out with 45% saturation ammonium sulfate. The resulting precipitate fraction was dissolved in a 0.02 M tris buffer solution, pH 7.9, containing 0.04 M sodium chloride and this solution was dialyzed overnight at low temperature against the same buffer soltuion. Using a column (2 cm in diameter and 80 cm in length) packed with 200 ml of DEAE cellulose (DE-52; Whatman Co.), the retentate was subjected to ion exchange chromatography in which an ionic strength gradient was established with 0.02 M tris buffer solutions, pH 7.9, containing 0.04 M to 0.15 M sodium chloride. Thus, a fraction eluted at a sodium chloride concentration of 0.04 M was recovered. This fraction was further precipitated with 50% saturation ammonium sulfate and the precipitate so formed was dissolved in deionized water. This solution was dialyzed and then freeze-dried to obtain 364 mg of a monoclonal antibody against bovine lactoferrin.

An enzyme-linked immunosorbent assey (ELISA method) revealed that the antibody was of the IgG type.

Preparation of an Affinity-Chromatographic Column

10–30 mg/ml, preferably 20 mg/ml or more, of the purified monoclonal antibody against bovine lactoferrin obtained in the above manner was mixed with an equal amount of a carrier for use in affinity chromatography (Affigel-10) and this mixture was stirred overnight at low temperature to bind the antibody to the carrier. After being washed several times with a 0.1 M sodium bicarbonate buffer solution, pH 8.0, containing 0.15 M sodium chloride, the carrier was mixed with an equal amount of 0.1 M ethanolamine adjusted to pH 8.0 with hydrochloric acid, and this mixture was gently stirred at room temperature for an hour to inactivate those functional groups on the carrier to which the monoclonal antibody against bovine lactoferrin was not adsorbed. Thereafter, the carrier was thoroughly washed with a PBS, containing 0.15 M sodium chloride and then packed into a column of suitable size to form an affinity-chromatographic column.

Separation and Purification of Bovine Lactoferrin 2 ml of the affinity gel formed in the above manner and having fixed thereto a monoclonal antibody against bovine lactoferrin was packed into a column having an internal diameter of 13 mm. The monoclonal antibody against bovine lactoferrin was fixed in an amount of 4.7 mg per milliliter of the affinity gel. After the affinity gel within the aforesaid column was thoroughly washed with PBS, a solution of 5.5 mg of crude bovine lactoferrin (60% pure) in 1 ml of PBS was passed through the column at a rate of 2.5 ml/min.

Then, the affinity gel within the column was washed with PBS to remove the non-adsorbed fraction. As a result, a peak corresponding to the impurities present in the sample solution was noted and the protein content of this fraction was 1.7 mg. Further, after the aforesaid affinity gel was thoroughly washed with a PBS, containing 0.5 M sodium chloride and then with a 0.15 M sodium chloride solution, the adsorbed bovine lactoferrin was eluted with an acetate buffer solution, pH 2.7, containing 0.15 M sodium chloride. This sequence of operations was carried out at room temperature. The resulting eluate fraction was adjusted to pH 7, dialyzed against deionized water and then freeze-dried to obtain 3.4 mg of bovine lactoferrin. The bovine lactoferrin thus obtained had a purity of 98% or greater and an iron-binding ability of 3.7 mg/g. Its recovery was 92%. Thus, as illustrated by this example, the affinity-chromatographic column used in the present invention makes it possible to recover bovine lactoferrin in high yield without causing any reduction in purity or iron-binding ability.

EXAMPLE 2

The affinity gel within the column used in Example 1 was thoroughly washed first with a PBS, containing 0.5 M sodium chloride and then with PBS containing 0.15 M sodium chloride. (Thus, the same column was repeatedly used in this and the following examples.) Thereafter, 19 ml of cow's skimmed colostrum was passed through the column in the same manner as described in Example 1.

In this case, however, the elution was carried out with a 0.001 M acetate buffer solution, pH 4.3, containing 0.15 M sodium chloride. As a result, there were obtained a fraction adsorbed to the affinity gel and a non-adsorbed fraction. The adsorbed fraction was worked up in the same manner as described in Example 1 to recover 4.0 mg of bovine lactoferrin. The recovered bovine lactoferrin had a purity of 98% or greater and its iron-binding ability was 2.7 mg/g.

EXAMPLE 3

After the used column was thoroughly washed in the same manner as described in Example 2, 25 ml of cow's raw skimmed milk was passed through the column in the same manner as described in Example 1.

As a result, there were obtained a fraction adsorbed to the affinity gel and a non-adsorbed fraction. The adsorbed fraction was worked up in the same manner as described in Example 1 to recover 3.0 mg of bovine lactoferrin. The recovered bovine lactoferrin had a purity of 98% or greater and its iron-binding ability was 2.5 mg/g.

EXAMPLE 4

After the used column was thoroughly washed in the same manner as described in Example 2, 25 ml of cow's pasteurized skimmed milk was passed through the column in the same manner as described in Example 1.

As a result, there were obtained a fraction adsorbed to the affinity gel and a non-adsorbed fraction. The adsorbed fraction was worked up in the same manner as described in Example 1 to recover 1.6 mg of bovine lactoferrin. The recovered bovine lactoferrin had a purity of 98% or greater and its iron-binding ability was 2.4 mg/g.

EXAMPLE 5

After the used column was thoroughly washed in the same manner as described in Example 2, 100 ml of cheese whey was passed thorough the column in the same manner as described in Example 1.

As a result, there were obtained a fraction adsorbed to the affinity gel and a non-adsorbed fraction. The adsorbed fraction was worked up in the same manner as described in Example 1 to recover 2.4 mg of bovine lactoferrin. The recovered bovine lactoferrin had a purity of 98% or greater and its iron-binding ability was 2.8 mg/g.

EXAMPLE 6

After the used column was thoroughly washed in the safe manner as described in Example 2, 100 ml of pasteurized cheese whey was passed through the column in the same manner as described in Example 1.

As a result, there were obtained a fraction adsorbed to the affinity gel and a non-adsorbed fraction. The adsorbed fraction was worked up in the same manner as described in Example 1 to recover 2.2 mg of bovine lactoferrin. The recovered bovine lactoferrin had a purity of 98% or greater and its iron-binding ability was 3.2 mg/g.

EXAMPLE 7

After the used column was thoroughly washed in the same manner as described in Example 2, 100 ml of a 1% WPC aqueous solution was passed through the column in the same manner as described in Example 1.

As a result, there were obtained a fraction adsorbed to the affinity gel and a non-adsorbed fraction. The adsorbed fraction was worked up in the same manner as described in Example 1 to recover 0.2 mg of bovine lactoferrin. The thus recovered bovine lactoferrin had a purity of 98% or more and its iron-binding ability was 3.0 mg/g.

What is claimed is:

1. A method for separating a highly pure form of bovine lactoferrin from cow's milk and purifying same which comprises preparing an affinity-chromatographic column by fixing a monoclonal antibody against bovine lactoferrin to an insoluble carrier; passing cow's milk or a solution of bovine lactoferrin derived from cow's milk through the affinity-chromatographic column; and then eluting the bovine lactoferrin adsorbed to the affinity-chromatographic column.

2. A method as claimed in claim 1 wherein the monoclonal antibody against bovine lactoferrin is produced by a hybridoma obtained by fusing spleen lymphocytes from a bovine lactoferrin-immunized mouse with mouse myeloma cells.

3. A method as claimed in claim 1 wherein the affinity-chromatographic column is prepared by fixing a monoclonal antibody against bovine lactoferrin to a carrier consisting of an affinity gel.

4. A method as claimed in claim 1 wherein the bovine lactoferrin adsorbed to the affinity-chromatographic column is eluted at a pH of 4.7 or less and the pH of the eluted bovine lactoferrin fraction is imxediately returned to neutrality.

5. A method as claimed in claim 4 wherein the column is eluted at a pH of 4.3 to 2.7.

* * * * *

UNITED STATES PATENT OFFICE
CERTIFICATE OF CORRECTION

Patent No. 4,668,771           Dated May 26, 1987

Inventor(s) Kawakami et al

It is certified that error appears in the above-identified patent and that said Letters Patent are hereby corrected as shown below:

Column 5, line 9, change "dispered" to --dispersed--.

Column 7, line 43, change "speen" to --spleen--.

Signed and Sealed this

Twenty-second Day of September, 1987

Attest:

DONALD J. QUIGG

Attesting Officer        Commissioner of Patents and Trademarks